United States Patent [19]

Krieg et al.

[11] Patent Number: 4,851,340
[45] Date of Patent: Jul. 25, 1989

[54] STRAINS OF BACILLUS TOXIC TO COLEOPTERA

[75] Inventors: Aloisius Krieg, Darmstadt; Alois M. Huger, Darmstadt-Eberstadt; Wolfgang Schnetter, Bammental, all of Fed. Rep. of Germany

[73] Assignee: Boehringer Mannheim GmbH, Mannheim, Fed. Rep. of Germany

[21] Appl. No.: 195,511

[22] Filed: May 18, 1988

Related U.S. Application Data

[60] Division of Ser. No. 27,991, Mar. 13, 1987, Pat. No. 4,766,203, which is a continuation of Ser. No. 681,918, Dec. 14, 1984, abandoned.

[30] Foreign Application Priority Data

Dec. 21, 1983 [DE] Fed. Rep. of Germany ....... 3346138

[51] Int. Cl.$^4$ .............. C12R 1/07; A61K 37/02; A01N 63/00; A01N 25/12
[52] U.S. Cl. ................................ 435/68; 435/70; 435/832; 424/93
[58] Field of Search ............. 435/68, 70, 832; 530/350, 858; 424/405, 93, 84; 514/2, 21

[56] References Cited

U.S. PATENT DOCUMENTS 4,764,372 8/1988 Herrnstadt et al. .............. 435/832

FOREIGN PATENT DOCUMENTS

WO88/08880 11/1988 PCT Int'l Appl. .

OTHER PUBLICATIONS

The Prokaryotes, Chapter 136, The Genus Bacillus: Insect Pathogens, Krieg, pp. 1743–1755, 1981.
Krieg et al., Advances in Biotechnological Processes 3, pp. 273–290, 1984.
Ohba et al., *J. of Inv. Path.*, 47, 12–20 (1986), "Insect Toxicity of *Bacillus thuringiensis* Isolated from Soils of Japan".

Primary Examiner—John Kight
Assistant Examiner—Nathan M. Nutter
Attorney, Agent, or Firm—Felfe & Lynch

[57] ABSTRACT

The present invention provides a new strain of microorganism, *Bacillus thuringiensis* of pathotype C, a process for obtaining a toxin therefrom and an insecticide for combating Coleoptera containing the new microorganism or a toxin obtained therefrom.

5 Claims, No Drawings

STRAINS OF BACILLUS TOXIC TO COLEOPTERA

This is a divisional of application Ser. No. 027,991 filed Mar. 13, 1987, now U.S. Pat. No. 4,766,203, which is a continuation of Ser. No. 681,918, now abandoned.

The present invention is concerned with a new strain of Bacillus, with obtaining a toxin therefrom and with a composition for combating Coleoptera.

Besides the chemical insecticides, bacterial insecticides have, for many years, been the subject of intensive investigation. In 1915, *Bacillus thuringiensis* (Bt) was described for the first time as the causative agent of flacherie in flour moth larvae. Up to the 1970's, all isolates of Bt belonged to a pathotype which was only effective against larvae of Lepidoptera. This type is called pathotype A. It includes not only *var. thuringiensis* but also *var. kurstaki* and *var. galleriae*, which are also used in practice.

In 1977, Goldberg and Margalit isolated from a sample originating from mosquito breeding sites in the Negev desert a strain which proved to be pathogenic towards larvae of various Nematocera (Diptera) and which was subsequently classified as *Bacillus thuringiensis var. israelenis* (Bti). This type is called pathotype B. In the meantime, this variety has also been used economically.

The advantage of bacterial insecticides is that they act very selectively on definite kinds of pests.

Thus, for example, U.S. Pat. No. 4,166,122 discloses an insecticide which contains as active component the variety *Bacillus thuringiensis var. israelensis* found by Goldberg. It is very clearly shown therein that this bacterial strain is pathogenic against mosquito larvae, whereas other organisms are not influenced.

However, there is still a need for bacterial insecticides which are active against other groups of pests.

Thus, according to the present invention, there is provided a new variety of *Bacillus thuringiensis* which is called *Bacillus thuringiensis var. tenebrionis* (Btt).

We have found that this strain has an insecticidal activity against certain types of beetles (Coleoptera) and especially against Chrysomelides, for example blue alder leaf beetle (Agelastica alni), as well as the Colorado beetle (Leptinotarsa decemlineato). Therefore, Btt is representative of a new pathotype, which is named pathotype C.

The present invention also provides a bacterial insecticide which, as active material, contains *Bacillus thuringiensis* of pathotype C and especially Btt or an insecticidally-active preparation or toxin obtainable therefrom.

The new variety was isolated from an infected pupa of the yellow meal worm (*Tenebrio molitor L.*, Coleoptera: Tenebrionidae). The pure culture is maintained at 25° to 30° C. on nutrient agar slants. The dry spores were frozen or freeze-dried in order to preserve them. The determination was based on morphological and biochemical characteristics.

On nutrient agar, Btt produces large, coarse, whitish colonies, the cells of which sporulate after 18 to 24 hours. The vegetative cell is flagellated and rod-shaped and measures approximately $1.0 \times 4-8$ μm. It reacts grampositively. The sporgangium contains, in addition to the subterminally-lying ellipsoidal spore ($0.8 \times 1.4-1.6$ μm), a parasporal crystal with a flat, plate-like form and usually with the shape of a parallelogram, rhombus or quadrat (about 0.8–1.5 μm edge length).

In the vegetative phase, facultative growth of the Bacillus also takes place anaerobically. On the other hand, the sporulation is strictly aerobic. Excellent growth and sporulation takes place at 25° to 30° C. Autoclaving for 15 minutes at 121° C. (corresponding to 1 bar overpressure) completely inactivates the spores and also the toxicity of the crystals. By means of UV irradiation at 254 nm, the spores are inactivated at an appropriate UV-dosage but not the toxic crystals.

The biochemical features of the vegetative cells are as follows: From decomposable carbohydrates, for example glucose, there are formed fermentation acid and acetyl methyl carbinol but no gas. Apart from glucose, mannose and saccharose are decomposed with acidification but not lactose, cellobiose, salicin, arabinose, xylose or mannitol. Aesculin is hydrolysed, as well as starch. The following enzymes can be detected: catalase, nitrate reductase and proteinase, whereas the following enzymes could not be detected: lysine decarboxylase, phenylalanine desaminase, urease and decithinase.

For production purposes on a laboratory scale, there was used a shake culture. 50 ml. amounts of medium were fermented in 250 ml. Erlenmeyer flasks. The medium used had the following composition: 0.5 % yeast extract, 0.5 % tryptone, 0.1 % glucose and 0.08 % monopotassium dihydrogen phosphate in tap water (pH 7.0). The selected fermentation temperature was 25° to 30° C. Subsequent to the sporulation of the culture, which can be monitored microscopically, the biomass was sedimented by centrifugation and washed with water or buffer. The spore-crystal preparation can be lyophilized.

The mode of action of Btt on Coleoptera larvae basically resembles that of pathotype A strains on Lepidotera larvae: feeding ceased within the course of a few hours and mortality occurred within a few days, depending upon the dosage. The toxic action depends upon the fact that the midgut epithelium cells are damaged by the toxic crystals dissolved in the gut juice. The damaged gut cells from the basement membrane and from one another and drift into the lumen of the gut. As a result of the breakdown of the gut barrier, bacterial cells penetrate into the hemocoel with the consequence of a fatal septicemia.

The new variety Btt, the prototype of which could be isolated from a dead T. molitor pupa, has been deposited with the German Collection of Microorganism under the number DSM 2803. Serological investigations revealed Btt (strain DSM 2803) as a member of serotype H 8a, 8b.

The new variety Btt, pathotype C, shows a selective insecticidal action on certain Coleoptera, for example on the blue alder leaf beetle and on the Colorado beetle. The action is much stronger in the case of the larvae than in the case of the imago. On the other hand, no effect was observed against larvae of Lepidoptera, for example the flour moth (*Ephestia kuhniella*) and the cabbage moth (*Plutella xylostella*) as well as against larvae of Diptera, for example the yellow fever mosquito (*Aedes aegypti*). The following Table summarises results of biotests.

TABLE

Toxic action of Btt on various Coleoptera, Lepidoptera and Diptera

| Species investigated | Dosage used (spore equivalents) | Toxic action |
| --- | --- | --- |
| Blue alder leaf beetle | $10^6/cm^2$ | + |
| Colorado beetle | $10^6/cm^2$ | + |
| Mediterranean flour moth | $2.5 \times 10^8/cm^3$ | − |
| Cabbage moth | $4 \times 10^7/cm^2$ | − |
| Yellow fever mosquito | $5 \times 10^6/cm^3$ | − |

The actual insecticidal principle of *Bacillus thuringiensis* of pathotype C is the parasporal toxic crystal. The crystal moiety can be isolated in that, in sporulated cultures, after lysis of the sporangia the crystals are separated from the cell residues and the spores and purified, for example via density gradients.

Molecular weight determination with Btt by aid of SDS-polyacrylamide gel electrophoresis, using the method of Laemmli (Nature, 227, 680/1970), revealed two main bands at approximately 65,000 D and approximately 70,000 D. Several bands of lesser intensity were found between 20,000 to 40,000 D. The toxin according to the present invention produces antibodies which show no cross reactivity with other toxins of pathotype A or B in an immuno-diffusion-test according to Ouchterlony.

The toxin is coded by a gen which is included in a plasmid. The toxin can also be produced in asporogenic mutants obtained by mutageneses with ethylmethanosulfonat. The ability to produce the toxin can be transmitted by plasmid or gen transfer to other varieties of Bt of other bacterial systems. The insecticidal effect is based on the presence of the plasmid coded toxin.

For use as an insecticide, *Bacillus thuringiensis var. tenebrionis* or an insecticidally-active preparation or toxin obtained therefrom is mixed in known manner with conventional additives (carrier materials, adhesion agents, wetting agents etc.) and converted into a form suitable for use. The insecticide formulated in this manner can be used, for example, in the form of a spray powder, a suspension, as a granulate or the like.

Preferably a purified, sporulated culture is used in form of a suspension with the addition of a wetting agent, for example 0.1% Citowet (BASF). $10^{12}$ to $10^{15}$, preferably $10^{13}$ to $10^{14}$ spores and an equivalent number of toxic crystals per hectacre are usually dispersed. For example in this way potato plants can be protected against Colorado beetles for 2 to 4 weeks. Additional treatments are necessary in order to protect the plants during the whole growth period. No effect against non target organisms, especially against entomophages and honey bees was observed.

What is claimed is:

1. Substantially pure Bacillus thuringiensis strain toxic to Cloeoptera and substantially non-toxic to Lepidoptera and Diptera.

2. *Bacillus thuringiensis var. tenebrionis* DSM 2803.

3. Substantially pure *Bacillus thuringiensis* strain toxic to Coleoptera, which strain produces a protein having a molecular weight of approximately 65 to 70 kilodaltons which is toxic to Coleoptera.

4. Substantially pure *Bacillus thuringiensis* strain toxic to Coleoptera, characterized by production of a parasporal crystal toxic to Coleoptera which contains a protein having a molecular weight of approximately 65 to 70 kilodaltons when said strain is cultured on nutrient agar at a temperature of 25° to 30° C.

5. Substantially pure Bacillus thuringiensis strain toxic to Coleoptera and substantially non-toxic to Lepitopdera and Diptera, which strain produces a protein having a molecular weight of approximately 60 to 70 kilodaltons and which is toxic to Coleoptera.

* * * * *